United States Patent [19]
Errico et al.

[11] Patent Number: 5,713,904
[45] Date of Patent: Feb. 3, 1998

[54] SELECTIVELY EXPANDABLE SACRAL FIXATION SCREW-SLEEVE DEVICE

[75] Inventors: Joseph P. Errico, Far Hills; Thomas J. Errico, Summit; James D. Ralph, Oakland, all of N.J.

[73] Assignee: Third Millennium Engineering, LLC, Summit, N.J.

[21] Appl. No.: 799,719

[22] Filed: Feb. 12, 1997

[51] Int. Cl.[6] .................................................. A61B 17/70
[52] U.S. Cl. ........................... 606/73; 606/72; 606/61
[58] Field of Search ............................. 606/73, 72, 61, 606/60; 411/15, 24, 32, 33

[56] References Cited

U.S. PATENT DOCUMENTS

| | | | |
|---|---|---|---|
| 3,896,504 | 7/1975 | Fischer | 606/73 |
| 4,611,581 | 9/1986 | Steffee | 606/73 |
| 4,716,893 | 1/1988 | Fischer et al. | 606/73 |
| 4,760,843 | 8/1988 | Fischer et al. | 606/73 |
| 5,489,210 | 2/1996 | Hanosh | 433/173 |

*Primary Examiner*—Guy V. Tucker
*Attorney, Agent, or Firm*—Joseph P. Errico, Esq.

[57] ABSTRACT

The present invention is a selectively expandable bone fixation screw-sleeve device which provides substantially greater holding strength in human bone than other bone screw devices. The sleeve element of this invention includes several embodiments, each having at least one corresponding screw element for selectively expanding a portion of the sleeve once it has been inserted into the bone. More specifically, in several embodiments, the sleeve includes a series of vertical slots in the end, or ends, of the cylindrical body of the sleeve. The slots define, therebetween, sections which are contiguous with the remainder of the cylindrical body, and which may rotate radially outward. In these embodiments, the sections are designed having a varying thickness, for example a single or double wedge profile, such that the insertion of the screw element into the sleeve deforms the shape of the sleeve by causing the sections to flair outward. In a different embodiment, the slots, and sections, are designed into the axially intermediate central portion of the cylindrical sleeve, and therefore flair outwardly therefrom upon insertion of a screw within the sleeve. As this invention is intended to provide improved fixation support for orthopedic implantation assemblies, each embodiment may further include means coupled or integral with the sleeve or screw for coupling an orthopedic implant to it.

2 Claims, 9 Drawing Sheets

SELECTIVELY EXPANDABLE SACRAL FIXATION SCREW-SLEEVE DEVICE

BACKGROUND OF THE INVENTION

1. Field of the Invention

This invention relates generally to a spinal fixation device. More particularly, the present invention relates to a screw-sleeve assembly for insertion into spinal bone such as for affixing orthopedic implantation structures to the spine.

2. Description of the Prior Art

The bones and connective tissue of an adult human spinal column consists of an upper portion having more than 20 discrete bones, and a lower portion which consists of the sacral bone and the coccygeal bodies. The bones of the upper portion are generally similar in shape, as will be more fully described hereinbelow with respect to FIGS. 1 and 2. Despite their similar shape, however, they do vary substantially in size in accordance with their individual position along the column and are, therefore, anatomically categorized as being members of one of three classifications: cervical, thoracic, or lumbar. The cervical portion, which comprises the top of the spine, up to the base of the skull, includes the first 7 vertebrae. The intermediate 12 bones are the thoracic vertebrae, and connect to the 5 lumbar vertebrae.

Figure 1:
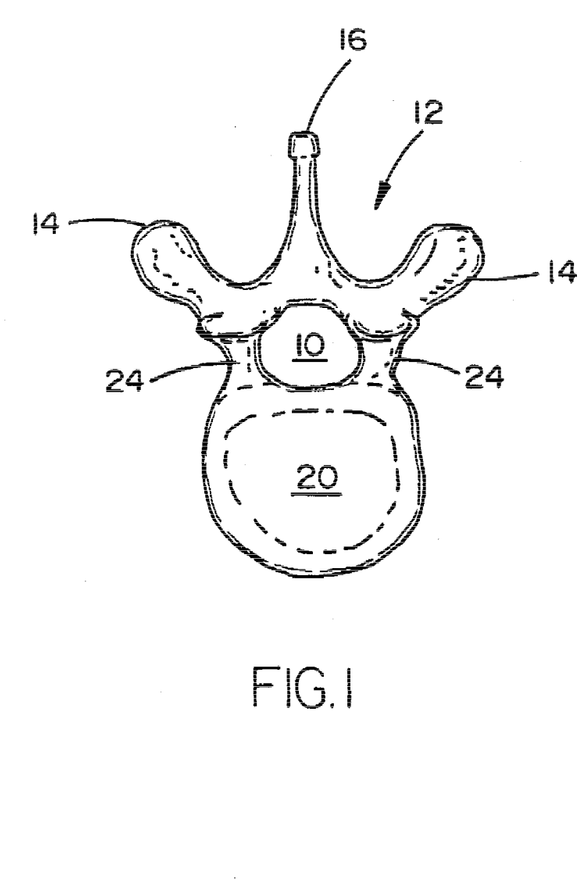
FIG. 1 is a top view of a vertebral bone characteristic of those of the cervical, thoracic, and lumbar spine.
Figure 2:
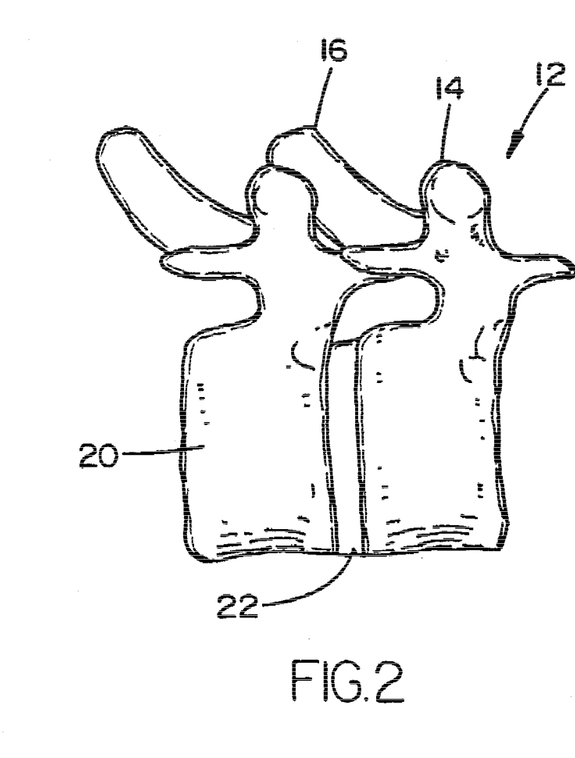
FIG. 2 is a side view of sequentially aligned vertebral bones, such as are found in the cervical, thoracic, or lumbar spine.

These similarly shaped bones vary in size, but are each similarly coupled to the next by a tri-joint complex. The tri-joint complex consists of an anterior disc and the two posterior facet joints, the anterior discs of adjacent bones being cushioned by cartilage spacers referred to as intervertebral discs. Referring now to FIGS. 1 and 2, top and side views of a typical vertebral body of the upper portion of the spinal column is shown. The spinal cord is housed in the central canal 10, protected from the posterior side by a shell of bone called the lamina 12. The lamina 12 has three large protrusions, two of these extend laterally from the shell and are referred to as the transverse process 14. The third extends back and down from the lamina and is called the spinous process 16. The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

Figure 3:
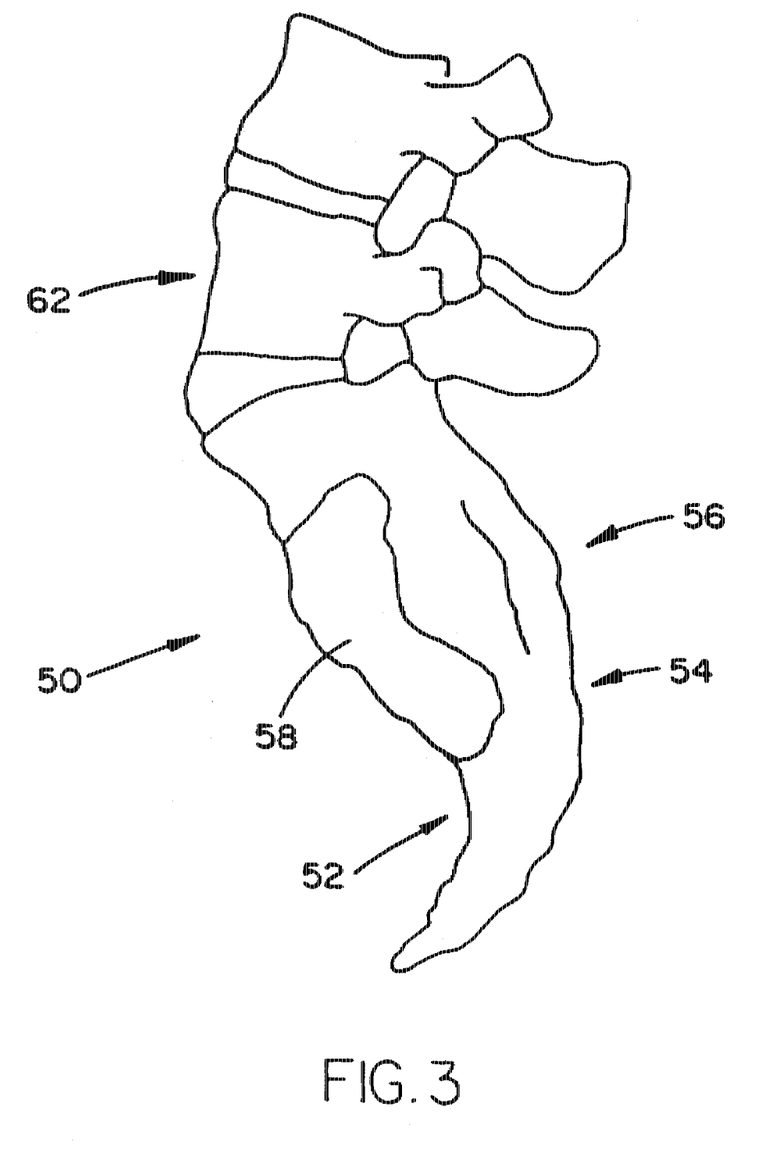
FIG. 3 is a side view of a sacral body.
Figure 4:
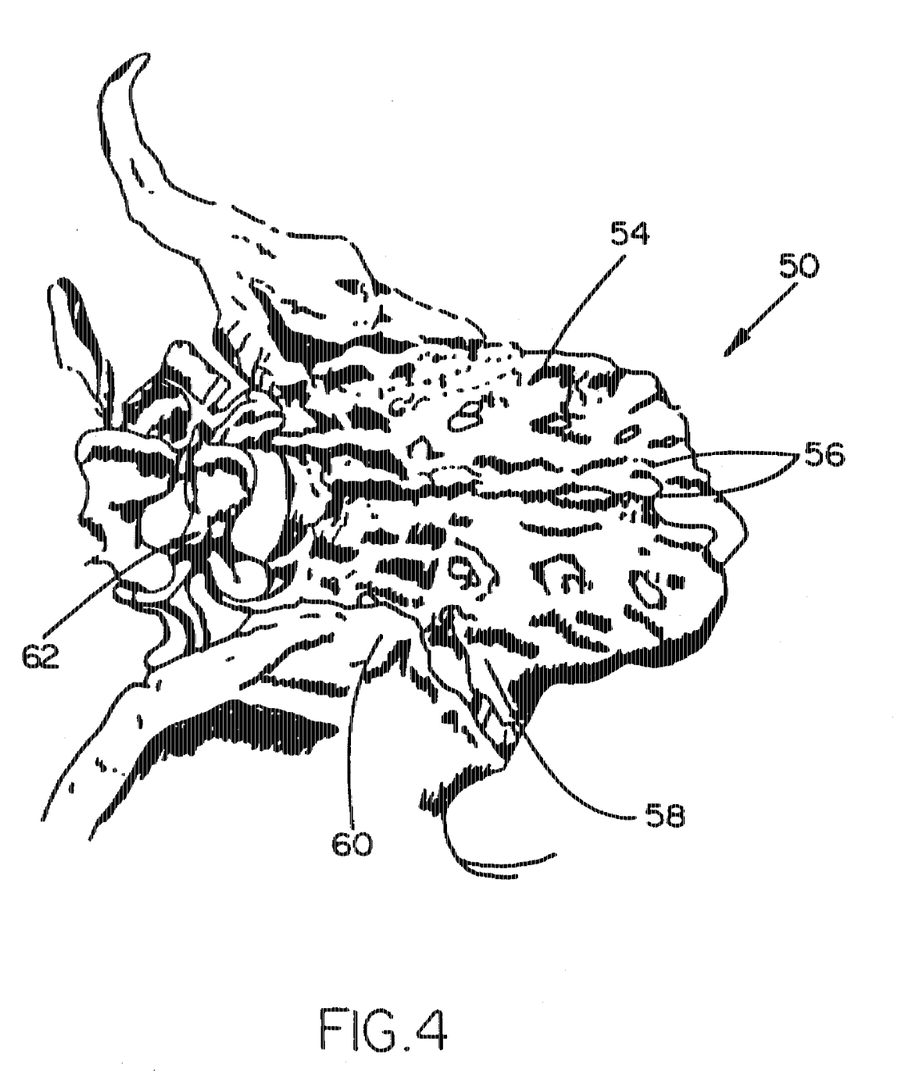
FIG. 4 is a perspective view of a sacral body as it is laterally coupled with the pelvis.

The lower portion of the spinal column, which extends into the hip region is primarily comprised of the sacral bone. This bone is unlike the other bones of the spinal column, in both shape and size. In fact, at birth humans have 5 disctinct sacral bones which begin to fuse together during childhood, and by adulthood have fully combined. FIGS. 3 and 4 show side and perspective views of a sacral bone connected to the lower lumbar vertebrae.

From the side, the sacral body 50 appears horn-shaped, having an anterior 52 and a posterior side 54. The perspective view, however, demonstrates the sacral bone to be more plate-shaped, having a thin, curvate profile. The posterior side 54 includes the sacral foramena 56 which are, in fact, the fused former lamina portions of the original acticulated sacral bones. Beneath the sacral foramena 56, the sacral roots of the spinal cord (not shown) are housed. The anterior 52 portion of the sacral body is, therefore, understood to be the fused former vertebral bodies of the originally articulated sacria bones. Extending laterally from the sacral plate are two, opposing, sacro ala 58, which are related to the transverse processes of the upper vertebrae. The sacro ala mate with the hip bones at the sacro-iliac joint 60. The sacro-iliac joint provides stabilization and support for the base of the spinal column, affording little if any rotational movement in adults. The top of the posterior portion of the sacral bone, the sacral foramena 56, couple with the lowest lumbar vertebra 62.

In its entirety, the spinal column is highly complex in that it houses and protects critical elements of the nervous system which have innumerable peripheral nerves and arterial and veinous bodies in close proximity. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back which needs to be immobilized, as well as the individual patient's anatomy, determine the appropriate surgical protocol and implantation assembly. In the lumbar spine, it is often necessary, or at least advantageous to use the larger sacral bone as the base structural support for the implant assembly. In the thoracic and cervical spine, posterior implantation assemblies are usually supported via screws which enter into the pedicle and extend into the vertebral body from the rear. Anterior implantation assemblies are generally supported by screws which enter into the vertebral bodies directly.

Because the spine is routinely subject to high loads which cycle during movement, primary concerns of physicians performing spinal implantation surgeries focus on screw pull-out and screw failure. Screw pull-out occurs when the cylindrical portion of the bone which surrounds the inserted screw fails. Screw failure occurs when the material of the screw breaks, often having been sheared in half. Advances in the strength of suitable screw materials rises, the mode of failure is continually shifting to screw pull-put. A bone screw which is implanted perpendicular to the plate is particularly weak because the region of the bone which must fail for pull-out to occur is only as large as the outer diameter of the screw threads. Screw pull-out often an additional danger in that it often leaves the bone into which the screw was implanted completely useless with respect to continued implant support.

Despite the value in designing screws which directly address the pull-out concern, the prior art is replete with examples of sacral and pedicle fixation devices which teach standard screw designs which do little to counter the risk of pull-out. For example, U.S. Pat. No. 4,569,338 to Edwards teaches a sacral fixation screw having a head which is matable with a hook, and, more relevantly, teaching a basic threaded shaft portion.

Similarly, U.S. Pat. No. 5,127,912 to Ray et al. teaches a sacral implant system comprising a set of sacral plates which may be affixed to the lumbosacral junction, in which a variety of screws are taught, each having a standard solid threaded shank.

The near universal use of standard style screw in the sacral bones is mirrored in the upper spine as well. For example, U.S. Pat. No. 5,024,213 to Asher et al. teaches a rod and fixation system for supporting a spinal column, wherein standard solid threaded screws are driven through the pedicle and into the vertebral body to provide the support for the entire assembly.

The failure of these prior fixation systems is the inadequacy of the screw elements which are intended for support. None are specifically designed to counter screw pull-out.

It is, therefore, the principal object of the present invention to provide a bone screw assembly which is specifically designed to counter screw pull-out.

It is also an object of the present invention to provide a bone screw which reduces the danger that screw pull-out will destroy the region of bone into which the screw has been implanted.

In addition, it is an object of the present invention to provide a bone screw design having a variable head such that the screw may be utilized in a wide variety of applications which are already known for spinal support and immobilization.

Other objects of the present invention not explicitly stated will be set forth and will be more clearly understood in conjunction with the descriptions of the preferred embodiments disclosed hereafter.

SUMMARY OF THE INVENTION

Human bone is generally comprised of a relatively thin shell of hard and strong material which is referred to as the corticle. The inner portion, which is referred to as the cancellous bone, is softer and less supportive. Unfortunately, because the corticle is thin, and is generally perpendicular to the direction of screw insertion, the majority of the holding strength of standard bone screws has come from the interface between their shafts (and threading) with the cancellous bone. It has been determined that the most important factor in screw fixation strength is its surface area (which is primarily a function of the outer diameter). This is especially true for screw designs which have a constant, or tapered, diameter, which cannot take advantage of the considerably stronger shell layer of corticle bone, as the diameter of the screw requires the hole in the shell portion to be as great or greater than the outer diamter of the screw.

The present invention, however, is designed to take advantage of the substantially stronger corticle bone shell, by presenting a larger diameter within the bone than the hole required for insertion. In addition, therefore, this design also has the advantage of presenting a greater diameter to the cancellous portion of the bone. These advantages have the combined effect of providing substantially more support strength than previous designs.

In general, the present invention comprises a screw and sleeve, wherein the sleeve is expandable by means of the insertion of the screw into the sleeve. A first embodiment provides a sleeve which is expandable only at its lower end. In a second embodiment the sleeve is expandable at its top and bottom ends. In a third embodiment the sleeve is designed to be expandable along its central portion.

More particularly, with respect a basic variation of the first embodiment, in its unexpanded state, the sleeve element is a cylindrical tube, having an external threading directed along its elongate axis. The bottom portion of the cylinder has a series of regularly spaced vertical slots which divide the bottom portion of the cylinder into separate articulated sections, which retain the general curvate shape of the cylinder, and extending downward from the upper portion.

The interior surface of the cylindrical tube of this basic variation also comprises an upper portion and a lower portion. The upper portion maintains a generally circular cross-section of constant diameter, having threading so that it may receive the screw. The lower portion, as described above, is characterized by vertical slots which divide the cylinder into separate vertical sections, which extend downward from the uninterrupted cylindrical upper portion.

The cross-sectional diameter of the lower portion, in contrast to the upper portion, is not constant. At the top of the lower portion, at the root of the slots which define the vertical sections, the cross-section of the tube is generally circular. The thickness of at least some of the separate vertical sections, however, become thicker, decreasing the diameter of the interior volume of the cylindrical tube in the elongate direction. In the axial direction, therefore, at least some of the sections cause a narrowing channel of the sleeve.

Implantation of the element into the bone requires only that a constant diameter hole be drilled into the receiving bone (such as a sacral body, pedicle, or vertebral body). The external threading provides for the sleeve to be driven into the hole by a suitable screwdriving means. Once positioned within the bone, the screw element may be driven into the sleeve.

The screw element of this basic variation of the first embodiment is a constant diameter threaded shaft, the diameter of which is equal to the inner diameter of the upper portion of the sleeve element. It is desirable to have a rounded tip, as it facilitates interaction with the lower sections. As the screw is driven into the sleeve it mates securely with the interior threading thereof.

As the tip of the screw is advanced into the lower portion of the sleeve, the narrowing of the interior of the sleeve, necessitates the application of an outward force against the thickened vertical sections in order for the screw to advance. This force, and the advancing screw tip, causes the vertical sections to flair outward, causing the lower portion of the sleeve to expand to a larger diameter within the bone.

In a second embodiment the sleeve element has vertically aligned slots, and correspondingly expanding sections, in both the upper and lower portions of the cylindrical tube, therein providing flairing sections at both ends of the cylinder. An central portion, intermediate of the two flairing ends, is an unslotted cylinder and provides the interior threading of the sleeve for mating with the screw threading. The lower flaring sections may be generally similar to those of the first embodiment, having an ever thickening profile with respect to the elongate direction of the cylinder. In order to receive a screw through the top of the sleeve, however, the flairing sections of the upper portion can be thickened only minimally. A variety of alternate designs provide for the flairing of the top articulated sections. For example, in a first variation, the top of the screw may be widened instead, so that insertion of the screw into the sleeve causes the flairing sections to expand.

In this second embodiment all of the top sections flair outward upon full insertion of the screw. It shall be understood that it may be highly desirable to drive the sleeve far enough into the bone that the flairing top sections extend outward into the cancellous bone which is directly beneath the corticle shell. By inserting the sleeve in such a manner, the sleeve provides the added pull-out strength afforded by uncompromised corticle bone.

As will be described more fully with reference to the accompanying drawings, other aspects of this embodiment exist in which a number of the upper sections are intentionally left unexpanded after the screw is inserted. Variations having this design are particularly valuable for implant assemblies in which the top portion of the sleeve is designed to extend out of the bone, and have structural elements for coupling other elements thereto.

The third embodiment of the present invention comprises a sleeve which includes expanding sections which extend outward from the central portion. Variations of this embodiment may comprise flairing sections which expand outward and downward similarly to the lower sections of the first and second embodiments, or outward and upward as do the upper sections of the second embodiment, or both. More particularly, in this embodiment, the sleeve element includes circumferentially spaced longitudinal slots along its central portion. Sequential pairs of slots thereby defining therebetween articulated sections. To provide structural integrity and continuity along the axial direction, a number of these articulated sections are otherwise uncompromised, and therefore do not flair outward. The remaining articulated sections, however, may be sequentially connected by radial slots, for example along portions of the circumference which is proximal to the lower or upper ends (depending on the specific flairing direction) of the longitudinal slots. If the radial slots are formed at the lower ends, and the resulting sections are gradually thickened increasingly along the axial direction, they will flair outwardly and downwardly in correspondence with a screw being driven down the center of the sleeve.

Conversely, if the radial slots are formed at the upper ends of the longitudinal slots, and the resulting sections have profiles which thicken gradually to the center and then thin again at their bottom, the advancing screw will cause the sections to flair outward from the top. More specifically, the top of the flairing sections define a radial cross-section which is equal to that of the threaded portion of the tube. The thickness of the sections increases to a maximum (which narrows the channel through which the screw is to pass to a radius which is substantially smaller than that of the screw) at a point farther along the length of the section. The thickness of the section then narrows again toward its base, such that they may rotate outward about the root portion of the section.

It is understood that sleeve elements which comprise both types of expanding sections are anticipated by, and may be employed in conjunction with, the present invention.

The three basic embodiments of the invention, and variations thereof, having been introduced in this summary of the present invention, shall hereinbelow be more fully described with respect to the Figures.

DETAILED DESCRIPTION OF THE PREFERRED EMBODIMENT

While the present invention will be described more fully hereinafter with reference to the accompanying drawings, in which particular embodiments and methods of fabrication are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 5:
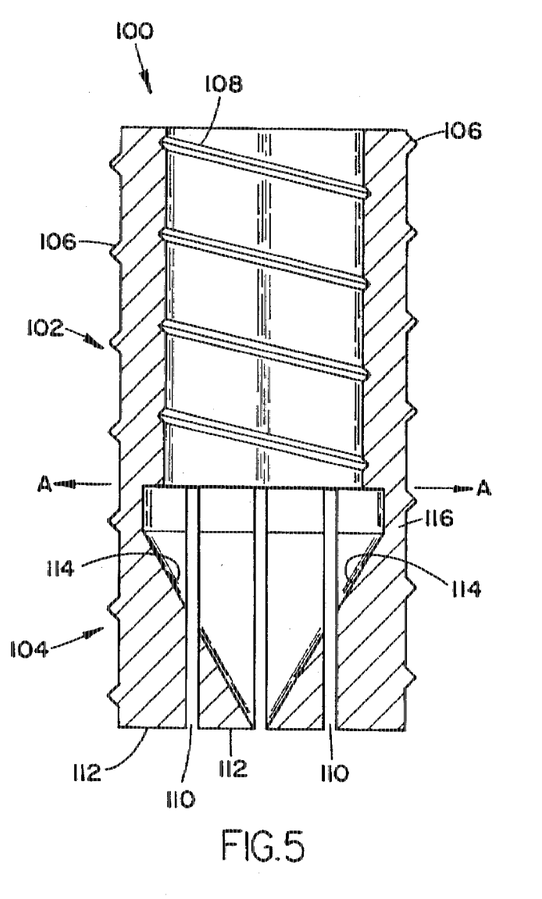
FIG. 5 is a side cross-sectional view of an expanding sleeve element of the present invention having lower sections which flair outward and downward as illustrated with phantom lines.

Referring now to FIG. 5, which is a cross-sectional illustration of the first embodiment of the present invention, a cylindrical sleeve element 100 is shown having upper and lower portions 102,104 respectively. Prior to the insertion of a screw into the sleeve 100, the exterior of the cylinder has a generally constant diameter. An external threading 106 is disposed on the outer surface of the sleeve 100. The threading 106 may be chosen from a variety of different types which have been used in the art of bone implantation.

The upper portion 102 of the cylindrical element 100 has a constant inner diameter, including a threading 108 which is mated with the specific screw which is to be inserted into the sleeve. The interior threading 108 of the upper portion is shown to be defined in the opposite sense from the external threading 106. This opposing thread design is desirable for certain applications such that subsequent tightening of a screw within the sleeve does not cause the sleeve to drive further into the bone in which it is disposed. It should be understood, however, that the anchoring functionality of the sleeve shall minimize concerns for undesired rotation of the sleeve.

The lower portion 104 of the sleeve includes a plurality of axial aligned slots 110 which extend vertically along the entire length of the lower portion 104, and which slots 110 divide the lower portion of the cylinder into separate articulated curvate sections 112. The interior surface 114 of each of the articulated curvate sections 112 of the lower portion 104 is sloped inward. This slope is illustrated in FIG. 5 as being a linear thickening of the sections along the axial direction, however, it shall be understood that equivalent functionality may be achieved with a non-linear axial narrowing of the inner volume. This sloped thickening provides a wedge profile to each of the sections 112.

In the embodiment shown in FIG. 5, the thickness of the circular cross-section of the lower portion 104 at its top (along line A----A), which is also the thickness of the sections 112 at the root 116 thereof, is thinner than the wall of the upper portion 102. This thinning of the root 116 provides a stress concentration zone of material around which the sections may rotate outward upon actuation as described hereinbelow. It is understood, however, that while it is desirable to provide a thinning at the root for the purposes of facilitating the outward rotation of the sections 112, it is necessary to chose the appropriate material of which to form the sleeve (or section elements) if such scoring is provided, so that the sections are not broken off by the force causing them to flair outward.

Figure 6:
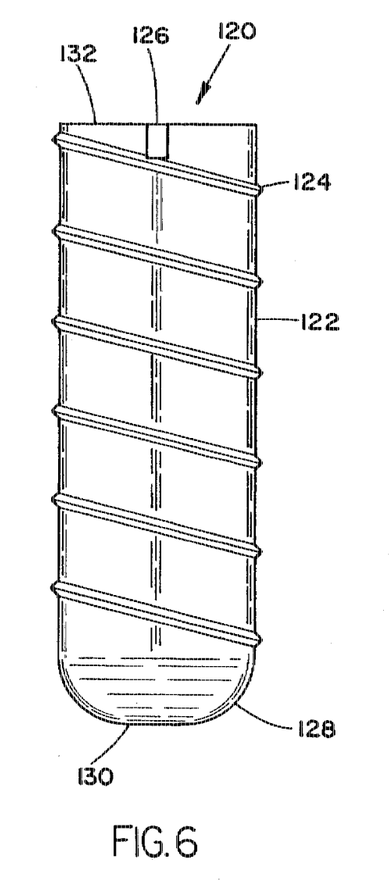
FIG. 6 is a side view of a screw which may be used to actuate the flairing sections of the expanding sleeve shown in FIG. 5.

Referring now also to FIG. 6, which shows a simple screw element 120 which actuates the flairing sections 112 upon its insertion into the sleeve 100. More precisely, the screw element 120, which has a generally cylindrical body 122, is inserted into the cylindrical opening of the top of the upper portion of the sleeve element 100, coaxially with the sleeve, such that the external threading 124 of the screw matably engage the internal threading of the upper portion 102. Continued advancement of the screw element 120 into the sleeve element 100, such as by the use of a screwdriving tool which may be inserted into a slot 126 formed in the top 132 of the screw, causes the screw to pass downwardly from the upper portion, and into the lower portion.

The lower end 130 of the screw is provided with a rounded edge 128, the rounded edge being ideally suited for advancing along the thickened, wedge profile, of the vertical curvate sections 112 of the sleeve 100. The advancement of the screw 120 into the lower portion 104 causes an expanding force to be applied against the inner surface 114 of the wedge profiled sections 112, and causes them to flair outward, rotating about thinner regions 116.

It is understood that the sleeve 100 or the screw 120 may further comprise, or be coupleable to, related structures which enable other implantation structures to be mated thereto. The purpose of this device is to provide a bone insert which provides an improved support to other orthopedic structures. The related structure may be integrally formed with, or coupled to, the sleeve or screw, for example, at the tops thereof which extend out from, or are disposed on the surface of, the bone in which the present device is inserted.

In operation, a pre-drilled hole is provided in the bone, into which it is desired that the sleeve and screw may be disposed. The hole may be pre-tapped, or the external threading 106 of the sleeve may include a self-tapping lead edge. In either event, and also the case in which no tapping is provided, the sleeve element 100 is screwed into the bone, to a desired depth. Once properly positioned, the screw element 120 is inserted into the sleeve, driven by a screwdriving tool, ultimately causing the rounded bottom end 130 of the screw 120 to expand the wedge shaped flairing sections 112 of the sleeve.

It is understood that the external threading 106 of the sleeve element is simply an expedient for the insertion of the sleeve into the bone. An embodiment of the sleeve, having an alternative exterior morphology to which bone may or may not adhere, which still comprises a cylindrical body having wedge shaped articulated sections formed in the lower portion thereof, which sections may be caused to flair outwardly and downwardly by the insertion of a screw, or other axially disposed member, for the purposes of providing superior fixation strength for a bone implantation structure, is equivalent to this embodiment for the purposes of the present invention.

Figure 7:
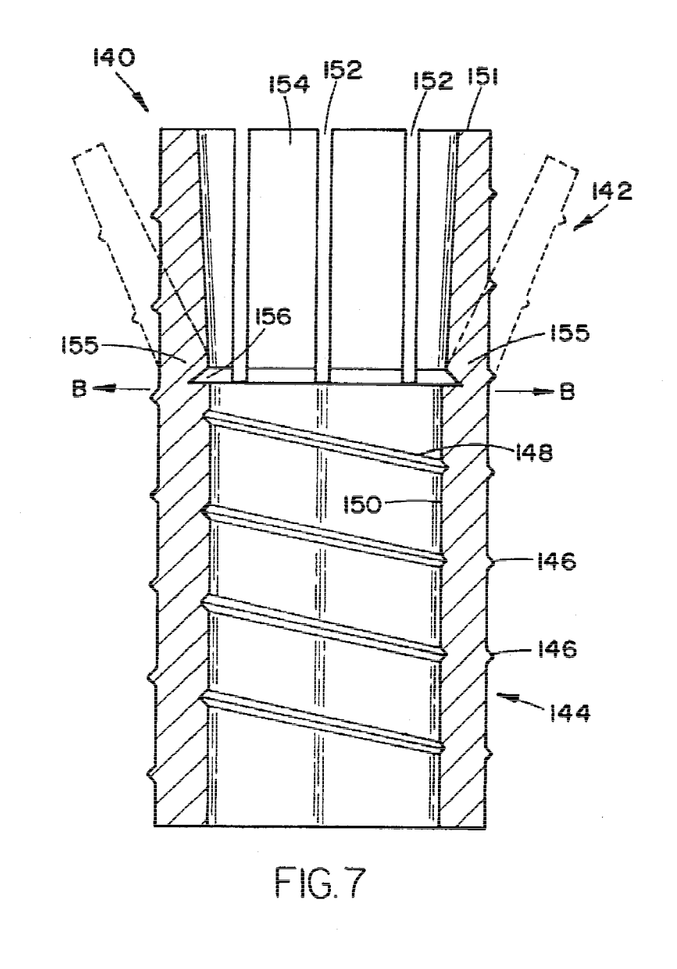
FIG. 7 is a side cross-sectional view of an expanding sleeve element of the present invention having upper sections which flair outward and upward as illustrated with phantom lines.
Figure 8:
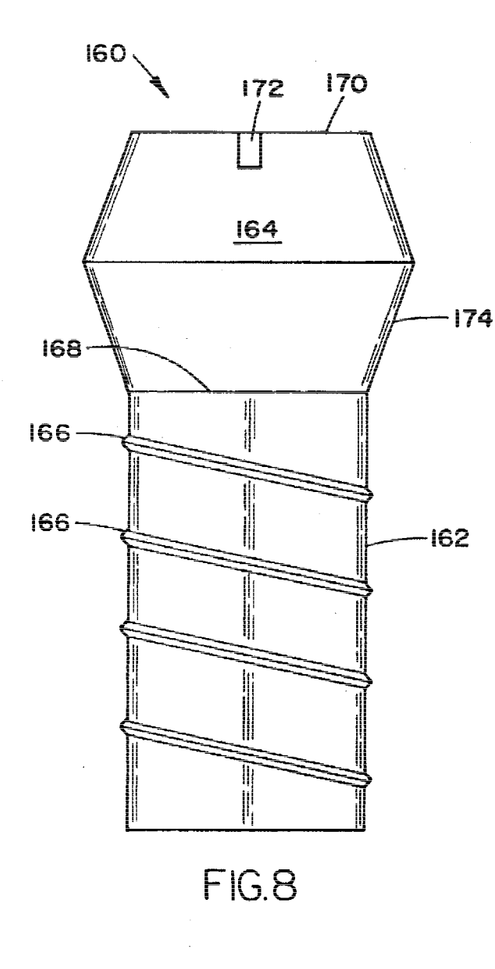
FIG. 8 is a side view of a screw which may be used to actuate the flairing sections of the expanding sleeve shown in FIG. 7.

Referring now to FIGS. 7 and 8, an alternative embodiment of the present invention is illustrated in a side cross-sectional view of the sleeve element 140, and a side view of the screw element 160 which is coupleable with the sleeve 140, respectively. The sleeve element 140 of this embodiment has a cylindrical body, having an upper and a lower portion 142,144. The entire length of the sleeve includes an exterior threading 146, oriented so that the sleeve may be screwably inserted into a receiving hole.

The lower portion 144, which has similar features to the upper portion of the embodiment shown in FIG. 5, has a generally constant inner radius, having an interior threading 148 disposed on the inner surface 150 thereof. This interior threading 148 is provided to couple with an exterior threading on the screw element 160 upon insertion of same into the sleeve.

The upper portion 142 of the sleeve 140 includes a series of vertically oriented slots 152 which extend from the top 151 of the upper portion 142 to the interface of the upper portion 142 and the lower portion 144. The slots 152 extend radially into the inner diameter of the sleeve, thereby defining individual, spaced apart, section elements 154 which are coupled together only in so far as the root of each section is continuously formed with the top of the lower portion 144 (at a position along the axial length of the sleeve B----B). This embodiment also includes a notch 156 disposed in the root portion 155 of each section 154. This notch 156 is desirable in that it provides a pivoting locus of relatively more flexible material, around which the sections may be caused to flair outward.

As compared with the sleeve 100 which is shown in FIG. 5, however, the sections 154 of this second embodiment are shown to be tapered slightly inward at the top, having a thickness at the root 155 which is, other than the notch 156, equivalent to the thickness of the continuous cylindrical wall 150 of the lower portion 144, and decreases linearly towards the top of the upper portion.

The screw element 160, which is designed for use with this embodiment, includes shaft portion 162 and a head portion 164. The shaft portion 162 includes an external threading 166 which is of a generally standard pitch and thickness as is useful for holding the screw 160 on the internal threading 148 within the sleeve 140. The head portion 160 has an axial length which is approximately equivalent to the axial length of the upper portion 142 of the sleeve 140, and has a generally circular radial cross-section. The radial cross-section of the head 160 varies from a radius equivalent to that of the shaft portion (and the inner surface 150 of the lower portion of the sleeve 160) at the interface of the head to the shaft, herein referred to as the base 168 of the head 160, to a maximum at a point intermediate along the length of the head 160, and which cross-section returns to the base 168 size at the top 170 of the head. The slanted profile of the head 164, therefore, may be envisioned as a pair of frusto-conical sections which have been coupled together along their wide cross-sectional surfaces; their narrow surface ends forming the top 170 and base 168 of the head element.

In operation, this embodiment is inserted into the bone receiving site in a similar fashion to the previously described embodiment. It is particularly desirable to position the sleeve deep enough within the receiving bone so that the flairing sections, when caused to expand via insertion of the screw 160 therein, flair outward beneath the corticle bone surrounding the hole. Once the sleeve 140 has been appropriately positioned in the bone, the screw 160 is inserted into the sleeve 140, and advanced thereinto, along interior threading 148 of the sleeve, via a screwdriving tool which couples to the screw 160 at slot 172.

Continued advance of the screw 160 into the sleeve 140 causes the head 164 to enter the upper portion of the sleeve. The outwardly slanted profile 174 of the bottom of the head comes into contact with the flairing sections 152, applying an expanding force to the sections as the screw continues to advance. Although the outwardly slanted profile 174 does not extend beyond an intermediate position along the axial extent of the head 164, the continued advance of the head increases the angular spread of the flaired sections 154 to a maximum once the base 168 of the head 164 reaches the bottom of the upper portion 142 (shown as line B—B).

Figure 9:
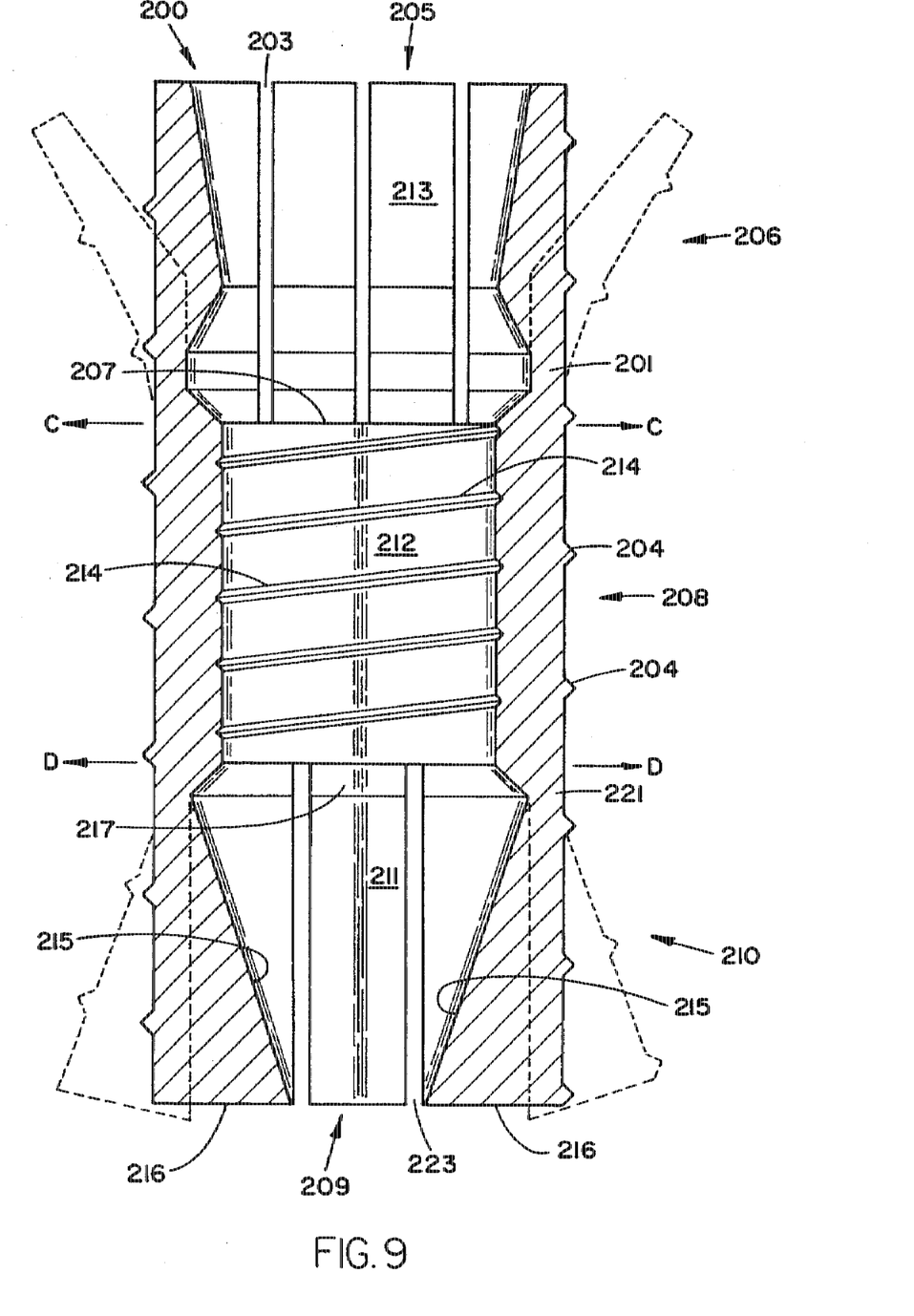
FIG. 9 is side cross-sectional view of an expanding sleeve element of the present invention having upper and lower sections which flair outward, the flairing extent being illustrated with phantom lines.
Figure 10:
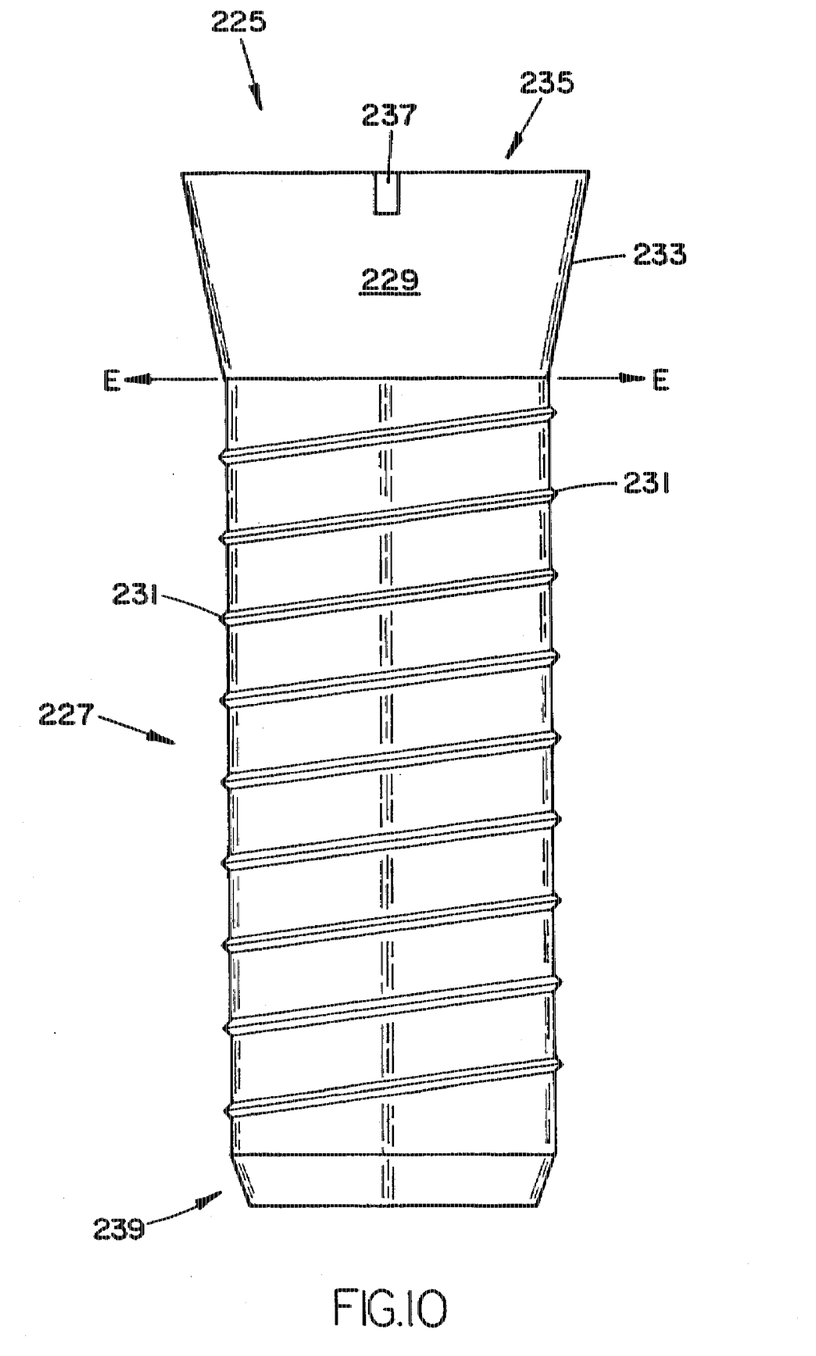
FIG. 10 is a side view of a screw which may be used to actuate the flairing sections of the expanding sleeve shown in FIG. 9.

An third embodiment of the present invention, comprising both upper and lower flairing sections 202,204, is shown in FIGS. 9 and 10 which show, respectively, a cross-sectional view of the sleeve element 200 and a screw element 225. The sleeve 200 of this embodiment is, again a generally cylindrical element, having an external threading 204, disposed on the outer surface thereof, for secure insertion into a bone. Unlike the sleeves described above, however, the sleeve 200 of the third embodiment is divided into an upper, a central, and a lower portion 206,208,210. The central portion 208 is a continuous cylinder, having a constant diameter inner channel 212. The inner channel 212 further includes a threading 214.

The upper and lower portions 206,210 of the sleeve 200 are designed to flair outward upon the insertion of a corresponding screw 225, in a manner which is similar to the correspondingly functioning portions of the previously described embodiments. More specifically, the upper and lower portions 206,210 include a plurality of vertically aligned slots 203,223, respectively, which extend along the axial direction of the sleeve 200. The slots 203 of the upper portion 206 extend from the top 205 of the sleeve to the interface 207 of the upper and center portions 206,208 (shown in the Figure as line C—C). The slots 223 of the lower portion 210 extend from the bottom 209 of the sleeve to the interface 217 of the lower and center portions 210,208 (shown in the Figure as line D—D).

The slots 203 extend into the inner channel 213 of the upper portion, defining therebetween sections 202, which are thereby rendered contiguously the cylinder only at the interface 207, by root regions 201. The thickness of the root region of the sections 202 of the upper portion 206 is thinned so that an outward force applied to the inner surface of the upper portion 206 will cause the flairing sections 202 to expand outward. The axial thickness of the remainder of the section 202 is tapered from a thickness above the root 201, from a thickness which is equivalent to the thickness of the walls of the central portion 208, to the top 205.

The slots 223, which are similar to those in the upper portion 206, extend into the inner channel 211, defining therebetween flairing sections 216 which are contiguous with the central portion 208 at root regions 221 thereof. The root region 221 of the sections 216 are thinned to provide flexing regions around which the corresponding section 216 may rotate when an expanding force is applied to inner surfaces 215 of the lower portion 210. The inner surfaces 215 of the sections 216 of the lower portion 210 are increasingly thick, from the thinned root region 221 to the lower end 209 of the sleeve 200, thereby providing a wedge profile to the sections. The thickened ends of the sections 216 cause a narrowing of the inner volume 211, such that the insertion of a constant diameter screw causes the sections 216 to flair outward.

The screw element 225 includes a shaft 227 and a head 229. The screw 225 has a threading 231 disposed along the length of the shaft 227, which shaft 227 has a generally constant diameter. The threading 231 preferably has a corresponding pitch and thread design so that it may be screwed into the sleeve 200 and mate with the threading 214 on the inner surface of the sleeve 200. The head 229 of the screw comprises a cap of a frusto-conical shape, and is contiguous with the shaft 227 (the interface of the head and the shaft being shown in FIG. 10 along line E—E). The narrow end of the frusto-conical cap has a diameter portion which equivalent in diameter to the diameter of the the shaft 227. The sides 233 of the head 229 expand outward to their maximum at the top surface 235 of the head.

As stated previously, with respect to the other embodiments described above, it is anticipate that this invention may be used in conjunction with a variety of implantation and fixation devices. Therefore it is intended and expected that the screw 225 or the sleeve 200 will include other features which are mounted or coupled thereto for purposes separate related but not limiting to the present invention.

In operation, the sleeve 200 is inserted, via screwdriving means, into a predrilled hole in the bone. Once properly and fully positioned, the screw 225 is inserted into the sleeve 200 and is advanced by a screwdriving means which mates with a corresponding recess 237 in the top surface 235 of the head 229. As the advancing end of the screw enters the channel 211 of the lower portion 210, the tapered end 239 engages the narrowing surfaces 215 of the wedge shaped sections 216, therein causing an outward flairing of the sections 216 as they rotate about thinned root regions 221.

As the lower wedge shaped sections 216 are flaired outward by the advancing end 239 of the screw 225, the expanding diameter sides 233 of the head 229 engage the flairing sections 202 of the upper section 206. The sides 233 of the head 229 provide an outward force which causes the expansion of the flairing sections 202.

Figure 11:
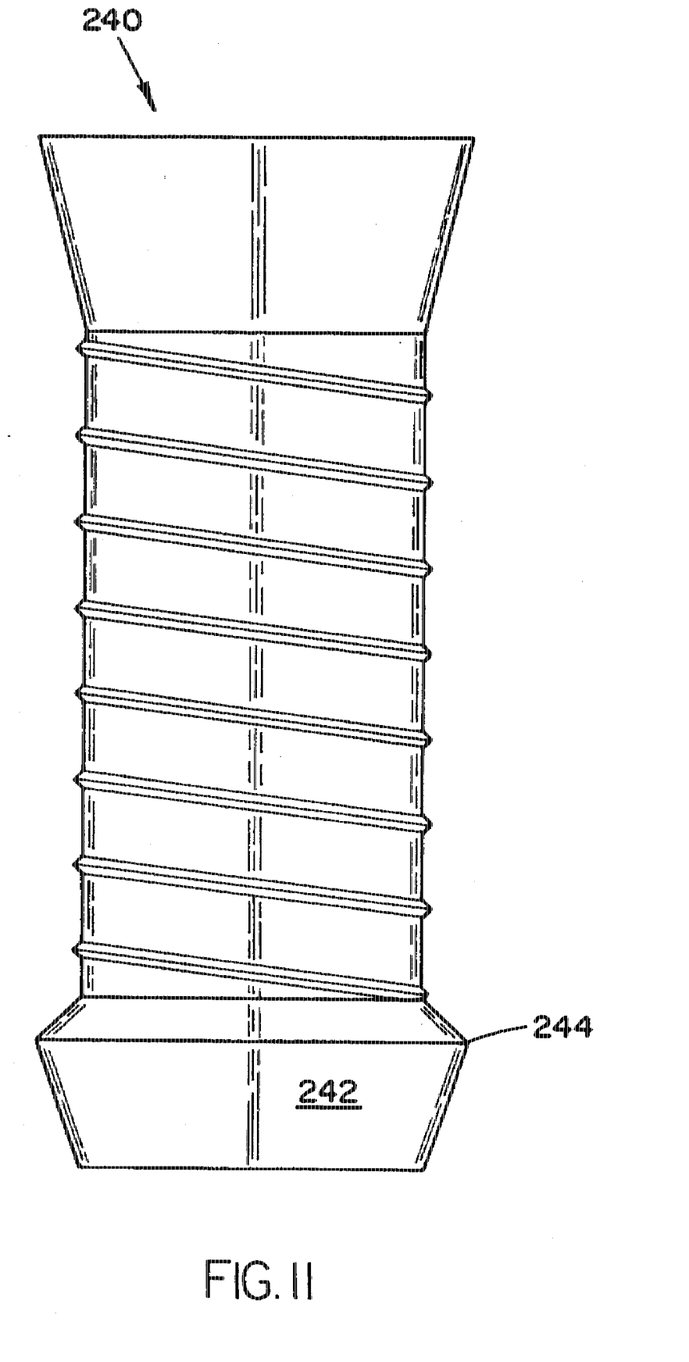
FIG. 11 is a side view of an alternative screw which may be used to actuate the flairing sections of the expanding sleeve shown in FIG. 9.

A variation of the screw of the third embodiment is shown in FIG. 11. Specifically, the lower end 242 of the screw 240 of this variation comprises a widened portion 244 which corresponds to diameter of the lower channel 211 at the root region 221 of the sections 216. The widened portion 244 has a diameter which is greater than the channel 212 of the sleeve. The screw 240, therefore, may be advanced into the sleeve 200, but is prevented from backing out by the widened portion (which cannot be removed through the central portion 208.

Figure 12:
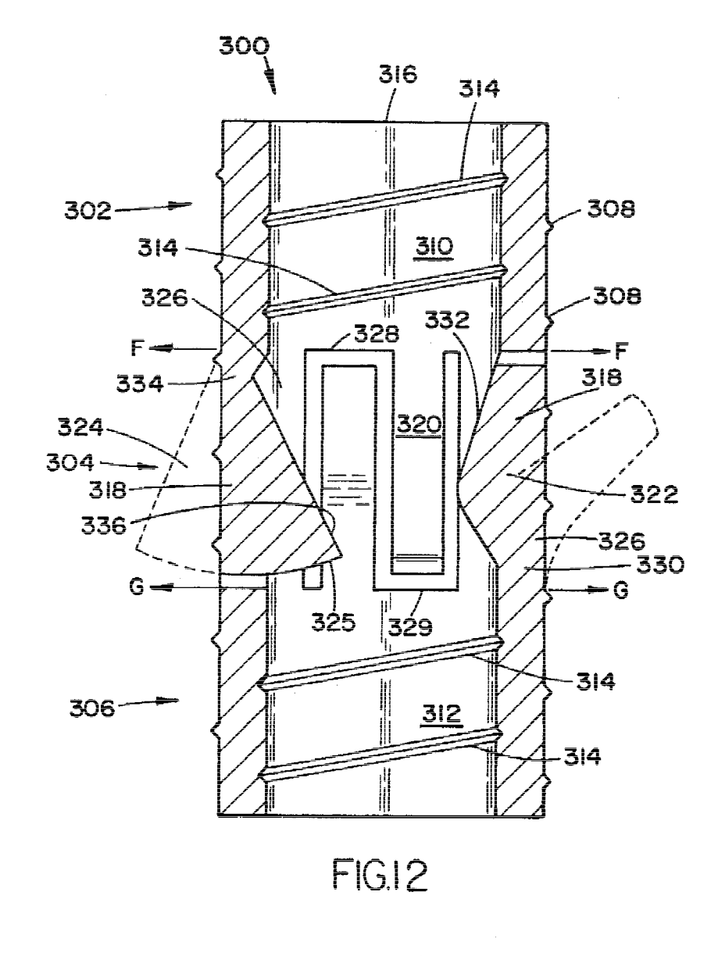
FIG. 12 is side cross-sectional view of another expanding sleeve element of the present invention having central sections which flair outward, the flairing extent being illustrated with phantom lines.
Figure 13:
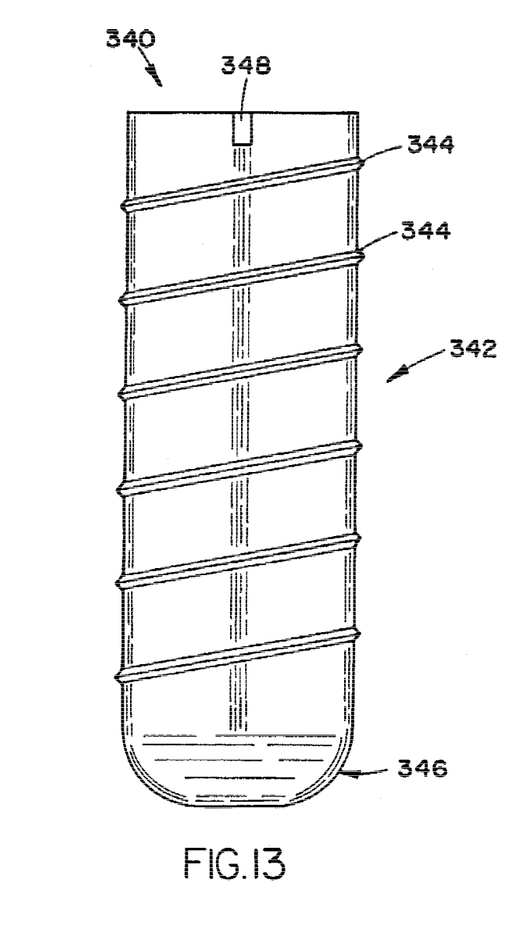
FIG. 13 is a side view of a screw which may be used to actuate the flairing sections of the expanding sleeve shown in FIG. 12.

Referring now to FIGS. 12 and 13, a fourth embodiment of the present invention is shown, first in a side cross-sectional view of the sleeve, and second in a side view of the screw. In this embodiment, flairing sections are disigned to expand outward from the central portion of the sleeve.

More specifically, the sleeve 300 of this embodiment includes upper, central, and lower portions 302,304,306, respectively. The external surface of the sleeve comprises a threading 308 for insertion of the sleeve into a bone. The upper and lower portions 302,306 of the sleeve further include similar constant diameter channels 310, 312, having an internal threading 314. The internal threading 314 is aligned so that a single screw may be inserted into the top 316 of the sleeve and simultaneously mate with the threading in both the upper and lower sections 302,306.

The central section 304 comprises regularly spaced vertically aligned slots 318. The slots 318 extend through the wall of the cylinder, into the inner volume 320 of the central portion 304, defining therebetween spaced sections 322,324, 326. Adjacent pairs of slots may be connected by a radially cut slot 328,329, at the interface of the upper and central portions (328, along line F—F, defining therebetween a first section 322), or at the interface of the lower and central portions (329, along line G—G, defining therebetween a second section 324). If adjacent pairs of slots are not connected by a radial slot, the (third) section 326 disposed therebetween is contiguous with the both the upper and lower portions 302,306. Therefore, three different types (first, second, and third) of sections exist in the central portion 304.

The first section 322, which is contiguous with the lower portion 306 only, comprises a notched root 330 about which the section 322 rotates upon application of an outward force against the inner surface 332 of the section. The first section 322 further comprises a thickened profile which begins at the root region 330 and widens to a thickness maximum at a point intermediate along its axial length, and then decreases to the thickness of the wall of the upper and lower portions 302,306, respectively. Such a profile, referred to as a double wedge profile, enables the first section to be flaired outward, about root 330, upon advancement of the corresponding screw through the sleeve.

The second section 324, which is contiguous with the upper portion 302 only, comprises a notched root 334 about which the second section 324 rotates upon application of an outward force against the inner surface 336. The second section further comprises a thickened, wedge profile, which begins at the root region 334 and widens to a maximum thickness at the free end 325 at the radially aligned slot 329. Such a wedge profile enables the second section to be flaired outward, about root 334, upon advancement of the corresponding screw through the sleeve.

The third sections 326, which are contiguous with both the upper and lower portions 302,306, and which connect the upper and lower portions 302,306, have a constant thickness which is preferably equivalent to the thickness of the walls of the upper and lower portions 302,306. It is understood that the third sections 326 may have a portion of threading 314 disposed on the inner surface thereof, for the purposes of continuing the threading of the screw into the sleeve, however, such additional disposition is not critical.

The screw element 340 of this fourth embodiment, as shown in FIG. 13, is similar to the screw 120 of the first embodiment. Specifically, the screw comprises an elongate shaft 342, having a threading 344 which is designed to smoothly mate the screw 340 to the sleeve 300, a rounded advancing end 346, and a screwdriving means recess 348 in the top. In operation, the sleeve is inserted into a pre-drilled hole in the bone to which implant affixation is desired. Once properly positioned, the screw 340 is advanced into the sleeve 300. As the rounded end 346 of the screw 300 advances into the central portion 304, it engages the inner surfaces 322,336 of the first and second sections 322,324, respectively. Continued advancement of the screw 340 causes the flairing sections to expand outward, into the surrounding cancellous bone, therein providing a much stronger fixation of the screw and sleeve thereto by virtue of a much larger diameter.

The fourth embodiment, as described with respect to FIGS. 12 and 13, includes both general types of flairing section (single wedge and double wedge profile sections) 322,324; the first, which expands outwardly with upwardly oriented sections having a double wedge profile; and the second, which expands outwardly with downwardly oriented sections having a single wedge profile, respectively. It is understood that, for a variety of applications, it may be determined that the specific use of the screw-sleeve device requires only one of the two types of section. In such a case, the variation of the fourth embodiment may include only one of the two types of flairing section 322 or 324. In all devices which are similar to the fourth embodiment, however, there must be third type sections 326, to connect the upper and lower portions 302,306.

While there has been described and illustrated several embodiments of a selectively expandable sacral fixation screw-sleeve device, it will be apparent to those skilled in the art that variations and modifications are possible without deviating from the broad spirit and principle of the present invention. The present invention shall, therefore, be limited solely by the scope of the claims appended hereto.

We claim:

1. A selectively expandable bone fixation screw-sleeve device, comprising:

an elongate member;

an elongate cylindrical sleeve having an upper, a central and a lower portion, each of said portions having an exterior surface and an interior surface, said interior surfaces of each of said portions together defining an interior channel extending axially through said sleeve, said interior channel further being capable of receiving therethrough said elongate member;

a plurality of axially aligned slots formed in said central portion of said elongate cylindrical sleeve, said slots extending from the exterior surface to the interior surface;

a plurality of radially aligned slots formed in said central portion, said slots extending from the exterior surface to the interior surface, each of said radially aligned slots connecting selected pairs of adjacent axially aligned slots;

a plurality of articulated sections, defined between sequential twos of said axially aligned slots, said articulated sections comprising first, second, and third types of sections, wherein said third type of section is defined between a pair of sequentially disposed axially aligned slots which are not connected by one of said radially aligned slots and therefore connect the upper and lower portions of the sleeve together, and wherein said first and second types of sections are defined between said selected pairs of adjacent axially aligned slots which are connected by one of said radially aligned slots, and wherein at least one of each of said first and second types of sections includes an interior conformation such that insertion of said elongate member through said interior channel of said elongate sleeve causes said first and second types of articulated sections to flair outward.

2. The selectively expandable bone fixation screw-sleeve device as set forth in claim 1, wherein the interior conformation which permits the first type of section portion to flair outward comprises a double wedge profile of said articulated section, and wherein the interior conformation which permits the second type of section to flair outward comprises a single wedge profile of said articulated section.

* * * * *